US009609511B2

(12) United States Patent
Vural et al.

(10) Patent No.: US 9,609,511 B2
(45) Date of Patent: Mar. 28, 2017

(54) DETERMINING A USER BASED ON FEATURES

(75) Inventors: Esra Vural, Potsdam, NY (US); Mark W Van Order, Corvailis, OR (US); Peter S Nyholm, Austin, TX (US); Stephanie Schuckers, Canton, NY (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 14/394,513

(22) PCT Filed: Jul. 31, 2012

(86) PCT No.: PCT/US2012/048946
§ 371 (c)(1),
(2), (4) Date: Oct. 15, 2014

(87) PCT Pub. No.: WO2014/021835
PCT Pub. Date: Feb. 6, 2014

(65) Prior Publication Data
US 2015/0111537 A1  Apr. 23, 2015

(51) Int. Cl.
| H04M 1/66 | (2006.01) |
| H04M 1/68 | (2006.01) |
| H04M 3/16 | (2006.01) |
| H04W 12/06 | (2009.01) |
| A61B 5/117 | (2016.01) |
| A61B 5/00 | (2006.01) |
| G06K 9/00 | (2006.01) |
| G06F 21/32 | (2013.01) |
| H04W 8/18 | (2009.01) |

(52) U.S. Cl.
CPC ............ *H04W 12/06* (2013.01); *A61B 5/0051* (2013.01); *A61B 5/117* (2013.01); *A61B 5/6898* (2013.01); *G06F 21/32* (2013.01); *G06K 9/00885* (2013.01); *H04W 8/18* (2013.01); *A61B 5/4869* (2013.01)

(58) Field of Classification Search
CPC ......... H04W 12/06; H04W 8/18; G06F 21/32; G07C 9/00158; A61B 5/6898; A61B 5/0051; A61B 5/117; A61B 5/4869; G06K 9/00885; G06K 9/00
USPC ....................................................... 455/411
See application file for complete search history.

(56) References Cited

U.S. PATENT DOCUMENTS

| 5,719,950 A | 2/1998 | Osten et al. |
| 6,765,470 B2 | 7/2004 | Shinzaki |
| 6,928,181 B2 | 8/2005 | Brooks |
| 2002/0049389 A1 | 4/2002 | Abreu |

(Continued)

OTHER PUBLICATIONS

Kwapisz, J.R. et al, "Cell Phone-based Biometric Identification", Sep. 27-29, 2004.

(Continued)

*Primary Examiner* — Tanmay Shah
(74) *Attorney, Agent, or Firm* — HP Patent Department

(57) ABSTRACT

A signal may be emitted by an emitter or transducer. The signal may be sensed by a sensor, such as an accelerometer. Features of a body part or portion may be one of detected, extracted, or constructed from the sensed signal. It may be determined whether the body part or portion matches that of a user, such as an authorized user, based on the features.

20 Claims, 10 Drawing Sheets

(56) References Cited

U.S. PATENT DOCUMENTS

| | | |
|---|---|---|
| 2005/0281439 A1 | 12/2005 | Lange |
| 2007/0255334 A1* | 11/2007 | Keimel .............. A61N 1/36007 607/40 |
| 2010/0183246 A1 | 7/2010 | King |
| 2010/0232653 A1* | 9/2010 | Muquit ................... G06F 21/32 382/116 |
| 2010/0253471 A1* | 10/2010 | Abe ........................ G06F 21/32 340/5.83 |
| 2011/0260830 A1 | 10/2011 | Weising |

OTHER PUBLICATIONS

Narayanasamy, G et al, "Ultrasound of the Fingers for Human Identification using Biometrics", Mar. 2008.
Korean Intellectual Property Office, International Search Report and Written Opinion for PCT/US2012/048946 dated Mar. 12, 2013 (12 pages).
The International Bureau of WIPO, International Preliminary Report on Patentability for PCT/US2012/048946, Feb. 12, 2015 (6 pages).
www.technicalpages.blogspot.com—Technical Papers—Biometrics, Feb. 9, 2008 (9 pages).

* cited by examiner

DETERMINING A USER BASED ON FEATURES

CROSS-REFERENCE TO RELATED APPLICATION

This application is a national stage application under 35 U.S.C. §371 of PCT/US2012/048946, filed Jul. 31, 2012.

BACKGROUND

Computing devices, such as smart phones and tablet computers, are becoming ubiquitous. It can be beneficial for these devices to have the ability to identify and/or authenticate a user. User identification can include determining which user is currently using the device. User authentication can include verifying the identity of the user. Providing user identification and authentication functionality can be challenging. For example, the components to provide this functionality can be expensive. Additionally, with respect to portable computing devices, the components can present a problem because they can take up significant space.

BRIEF DESCRIPTION OF DRAWINGS

The following detailed description refers to the drawings, wherein.

DETAILED DESCRIPTION

According to an embodiment, a computing device can include an emitter to emit a signal and a sensor to sense the signal after it has passed through a portion of a user's body. The device may also include an extractor to extract multiple features of the portion of the user's body from the signal. A classifier can be used to determine, based on the extracted features, whether the portion of the user's body corresponds to a model of the portion of the body used by the classifier. In such a manner, the user can be identified and/or authenticated.

User authentication and identification can be useful for many purposes. For example, portable computing devices can be lost or stolen. A user authentication feature on the device can prevent an authorized person from using the device in such an event. Additionally, sometimes multiple users use a single device. A user identification feature can enable the device to customize the device to each user. Sometimes user authentication and identification can occur simultaneously. In another example, another party can authenticate a user through the device. For instance, a bank may remotely instruct the device to perform an authentication of the user in order to verify the person's identity before granting electronic access to a bank account or before discussing account information over the phone. Further details of this embodiment and associated advantages, as well as of other embodiments, will be discussed in more detail below with reference to the drawings.

Figure 1:
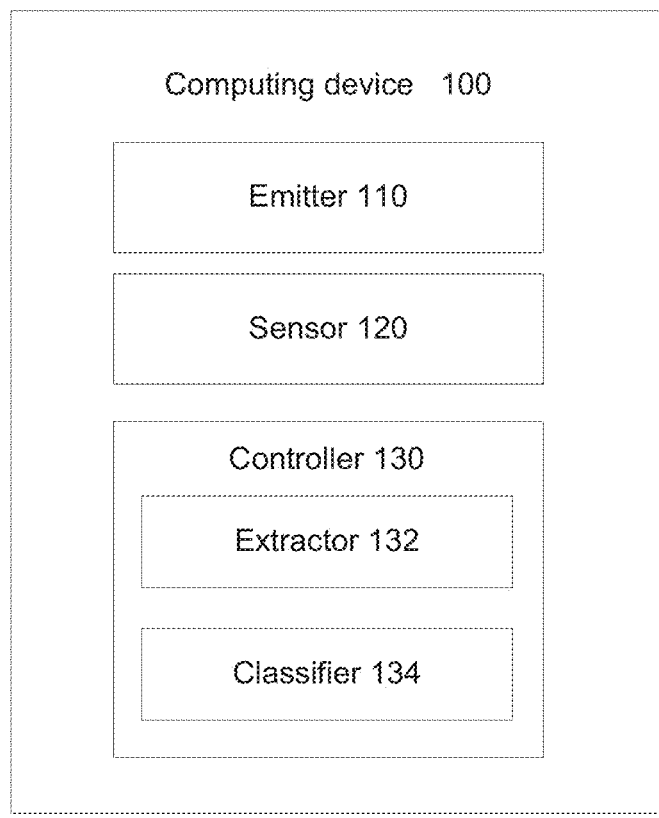
FIG. 1 illustrates a computing device for identifying or authenticating a user, according to an example.

Referring now to the drawings, FIG. 1 illustrates a computing device for identifying and/or authenticating a user, according to an example. Computing device 100 may be any of a variety of computing devices. For example, computing device 100 may be a portable computing device such as a cellular telephone, a smart phone, a media player, a tablet or slate computer, or a laptop computer. In some examples, computing device 100 can be a semi-portable or non-portable device, such as a desktop computer or a workstation computer.

Computing device 100 may include an emitter 110. Emitter 110 may emit a signal, such as an acoustic signal. The acoustic signal may range from a vibratory signal to an ultrasonic signal. Emitter 110 may include a transducer for emitting the signal. Emitter 110 may be configured to emit a signal in response to an instruction. For example, controller 130 may instruct emitter 110 to emit a signal.

Computing device 100 may include a sensor 120. Sensor 120 may sense a signal. For example, sensor 120 may be configured to sense a signal emitted by emitter 110. In an embodiment, sensor 120 may be an accelerometer. Sensor 120 may be selected based on its suitability for sensing signals in the acoustic range emitted by emitter 110. In one example, sensor 120 may be a micro-electro-mechanical system (MEMS)-based capacitive accelerometer. Such a sensor can have a low noise floor in a frequency range of 1-200 Hz and may be appropriate for sensing vibratory signals emitted by emitter 110. In other examples, sensor 120 may have a different frequency range.

Sensor 120 may be configured to sense a signal emitted by emitter 110 after the emitted signal has passed through a portion of a user's body. Portions of the user's body may include body parts or appendages such as a hand or an ear. Portions of the user's body may also include the user's organs, such as the user's heart.

Sensor 120 may be configured to sense after a predetermined period of time. For example, the predetermined period of time may be an amount of time after emitter 110 emits a signal. Waiting a predetermined period of time to sense the signal can give the signal time to travel through and/or reflect off the internal structure of the portion of the user's body. Accordingly, sensor 120 can sense the signal after it has been changed by the structure of the user's body rather than before such change.

The signal sensed by sensor 120 can be a transmitted signal, a reflected signal, or both. A transmitted signal can be a signal that is transmitted through the portion of the user's body without being reflected back by internal structure of the body. A reflected signal can be a signal that is transmitted through the portion of the user's body and is reflected back out of the body by internal structure of the body. The sensed signal may also be made up of both transmitted and reflected signals. As used herein, a signal that "passes through" a portion of the user's body can be a transmitted signal or a reflected signal. That is, reflected signals can be said to "pass through" a portion of the user's body even though they may not completely pass through the portion of the user's body (due to being reflected by the internal structure of the body).

Reflected signals can be sensed by sensor 120 even if sensor 120 is in the same housing as emitter 110. Some transmitted signals may be more easily sensed if the emitter 110 and sensor 120 are housed in separated housings. When the sensor 120 is configured to be separate from or separable from the emitter 110, sensor 120 can nonetheless be in communication with computing device 100 via a wired or wireless connection. Alternatively, the sensor 120 can be housed by a primary housing and the emitter 110 can be housed in a separate housing.

In an example, if the portion of the user's body is the user's hand, the transmitted signal can be the signal after it has been emitted by the emitter at one side of the hand and has passed through to the other side of the hand. In some examples, such as if one wants to sense a transmitted signal after it has entered at the palm side of the hand and exited on the knuckle side of the hand, the sensor 120 can be separate from the emitter 110 so that the sensor 120 can be placed on the opposite side of the hand from the emitter 110. In other examples, the sensor 120 can be in the same housing as the emitter 110, such as a smart phone housing, and still be capable of sensing a transmitted signal. For instance, if the portion of the body is the user's hand, the user may grip the smart phone in the palm of the hand so that the fingers and portion of the palm wrap around the sides of the smart phone. The sensor 120 may then sense the signal, which may have entered at the palm side of the hand and traveled lengthwise through the hand to exit on the palm side of the hand.

Identification and/or authentication of a user using the described emitter and sensor arrangement are possible because each user can have a unique internal structure of the body part/portion being examined. For example, where the body part is a hand, hand geometry (e.g., size and thickness), tissue-fat composition, and bone structure characteristics of a user's hand may attenuate or reflect the acoustic signal in a unique way.

Figure 2A:
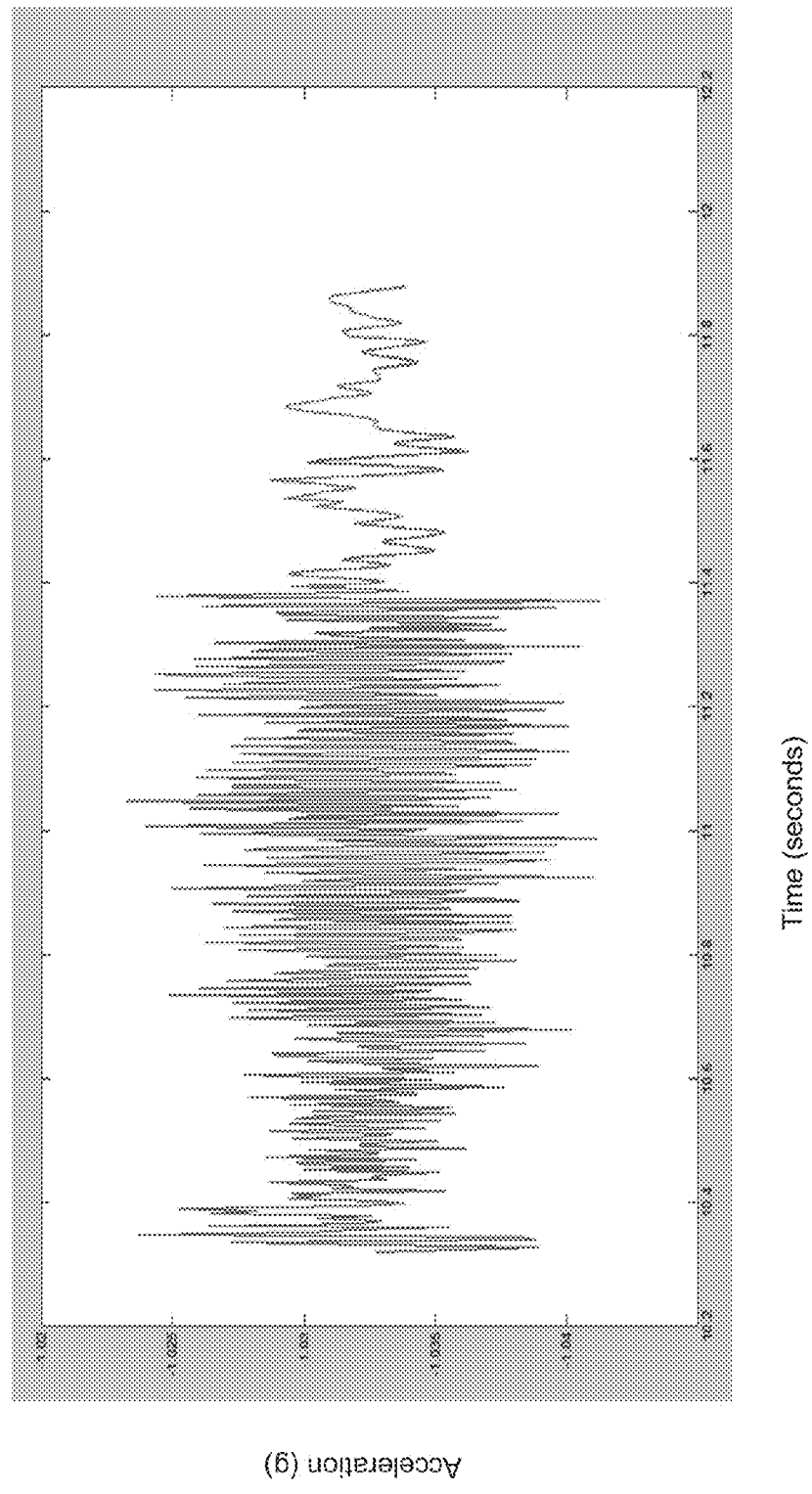
FIGS. 2(a)-(f) depict plots of signals transmitted through two users' hands and sensed by the device of FIG. 1, according to an example.
Figure 2B:
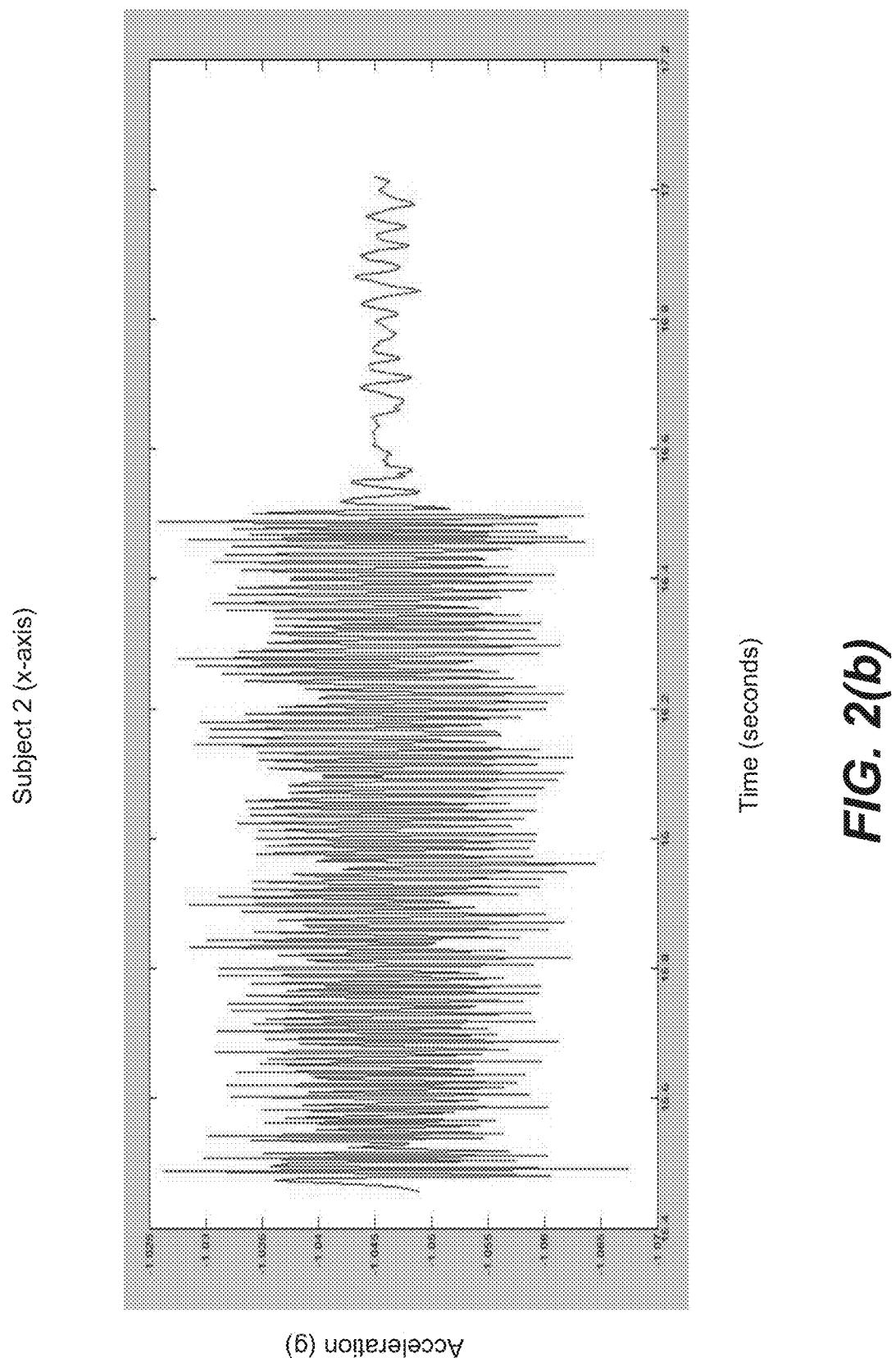
Figure 2C:
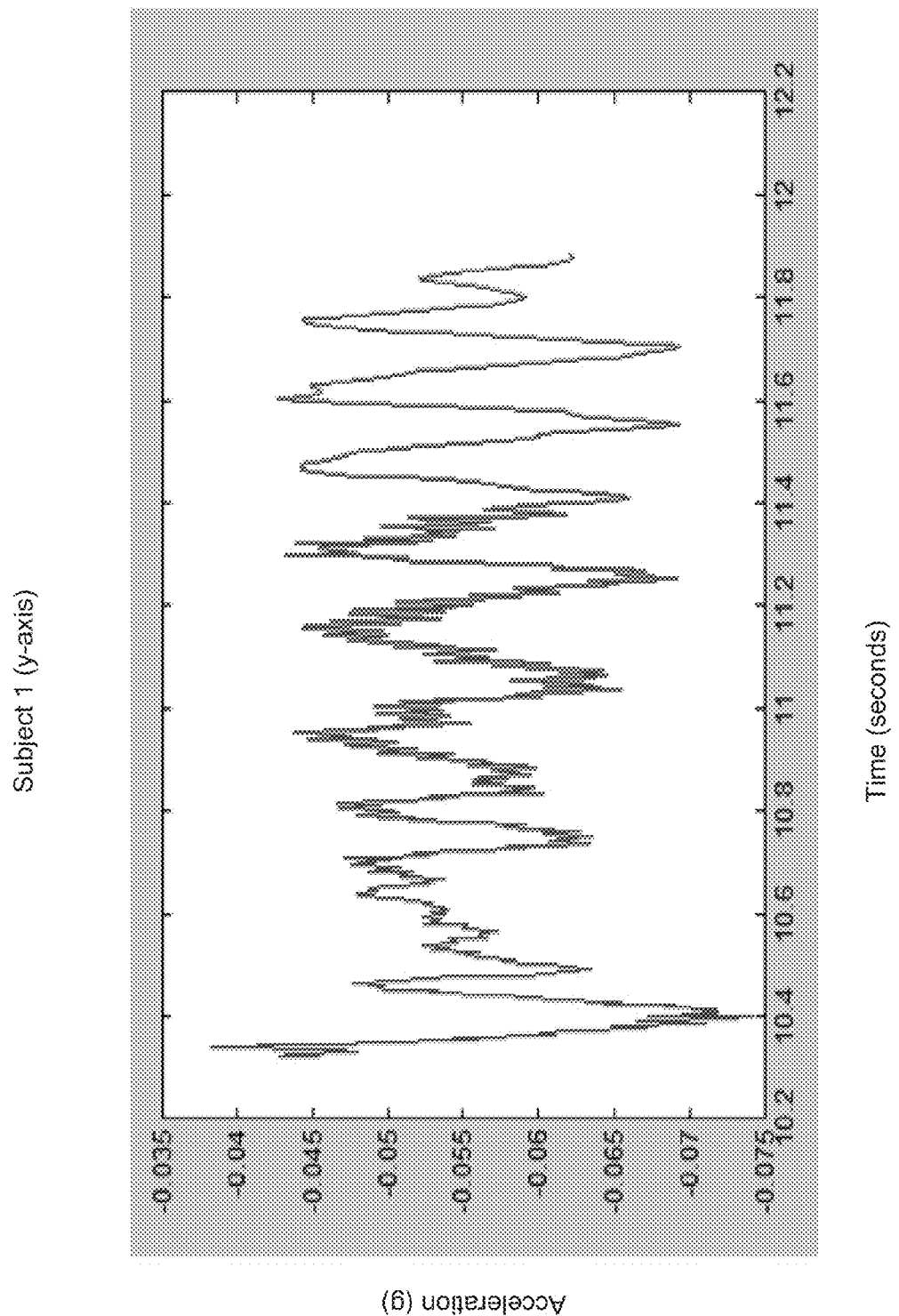
Figure 2D:
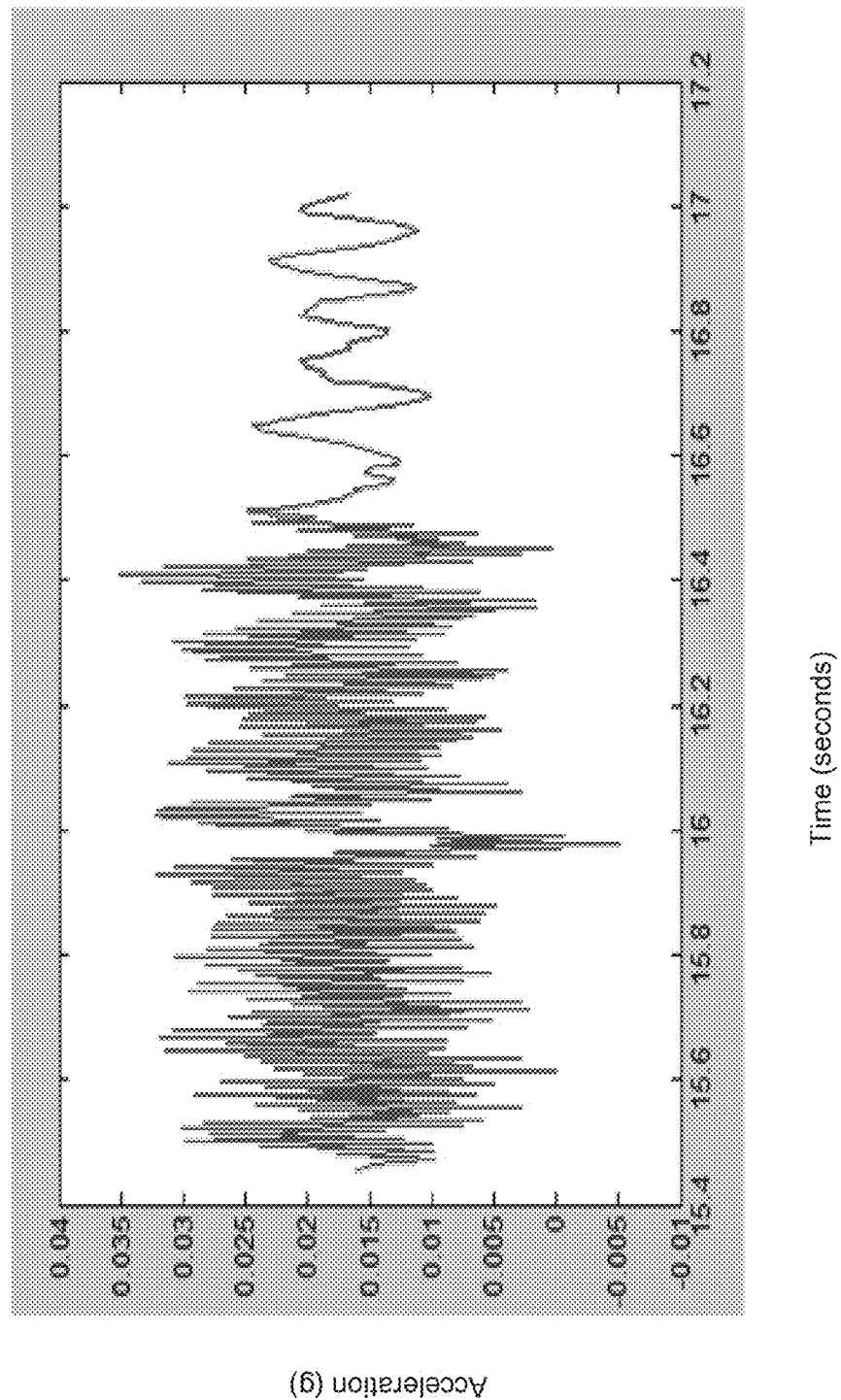
Figure 2E:
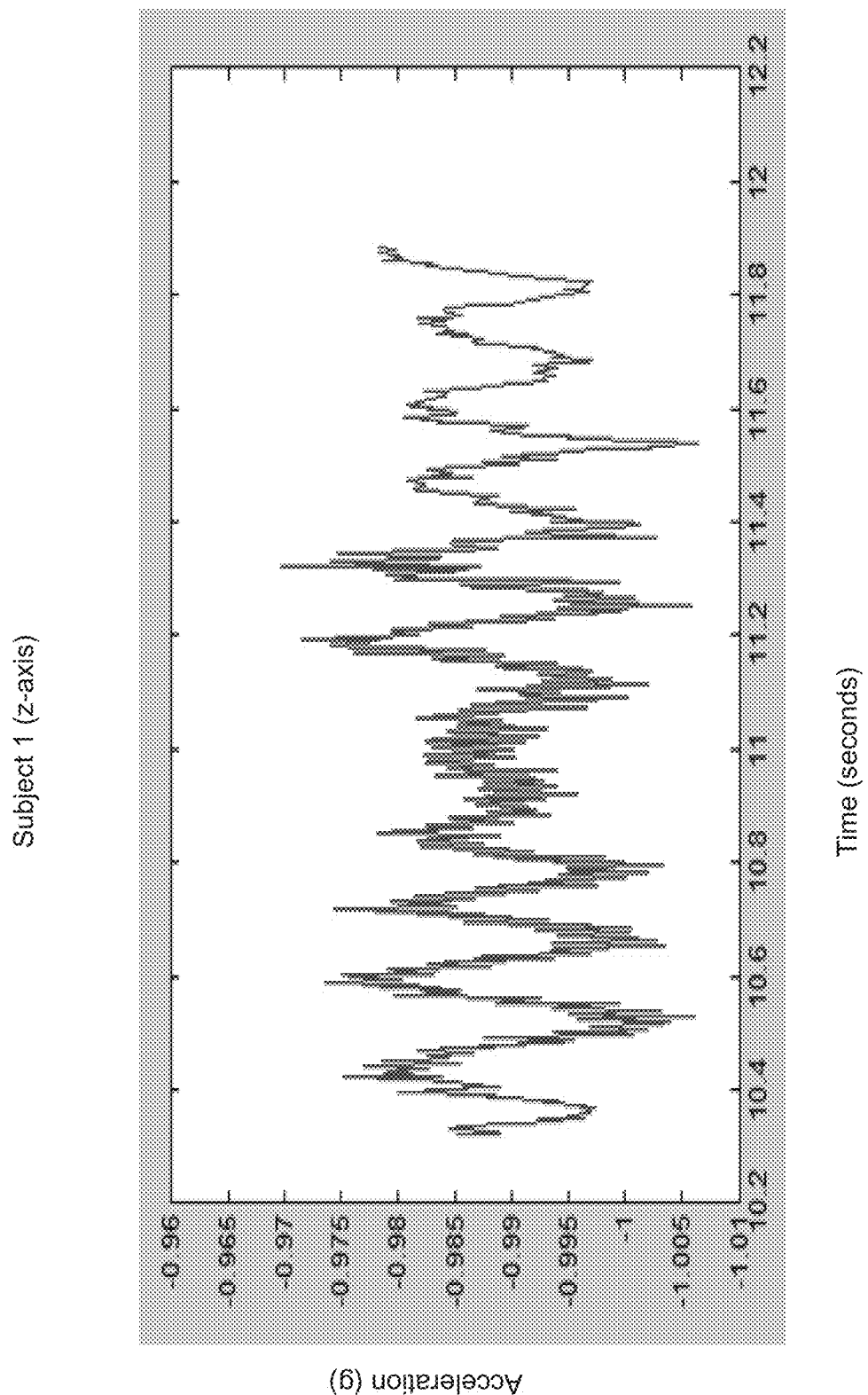
Figure 2F:
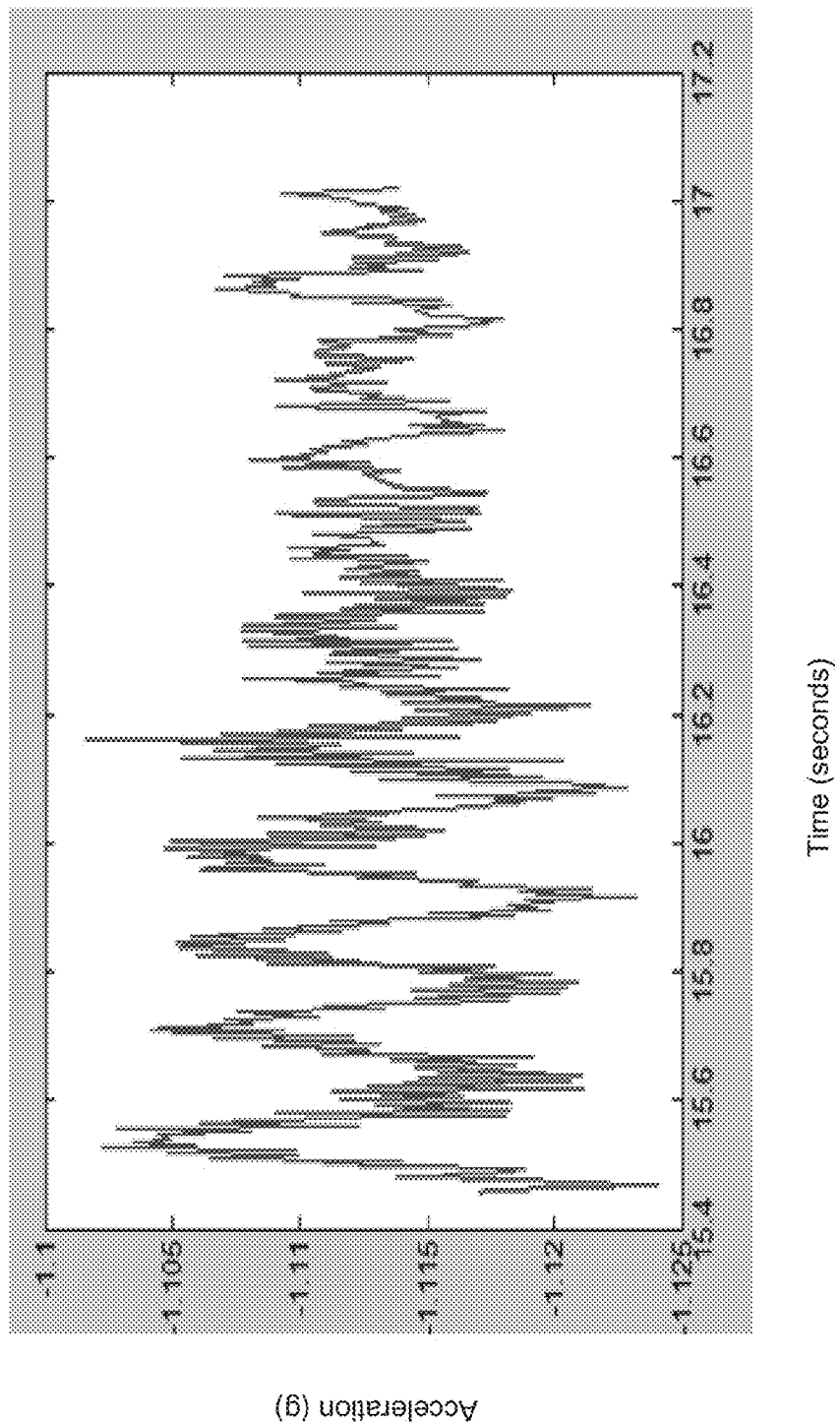

FIGS. 2(a)-2(f) illustrate plots of sensed signals for two users, subject 1 and subject 2. The body part being sensed was the users' hands and the same acoustic signal was emitted for each user for a duration of about 2 seconds. The signal was sensed using a 3-axis micro-electro-mechanical system (MEMS)-based capacitive accelerometer. FIGS. 2(a) and 2(b) depict the sensed signal for the x-axis of the sensor, FIGS. 2(c) and 2(d) depict the sensed signal for the y-axis of the sensor, and FIGS. 2(e) and 2(f) depict the sensed signal for the z-axis of the sensor. Visual evaluation of the plots reveals different sensed signals for each user, in line with the different internal structure of their hands. The pattern recognition techniques described below can be used to evaluate the sensed signals and classify them.

Computing device 100 may include a controller 130 having an extractor 132 and a classifier 134. Controller 130 may include a processor and a memory for implementing the extractor 132 and classifier 134, each of which may be software modules stored on the memory and executed by the processor. A software module may be a computer program comprising machine-executable instructions. The processor may include at least one central processing unit (CPU), at least one semiconductor-based microprocessor, at least one digital signal processor (DSP) such as a digital image processing unit, other hardware devices or processing elements suitable to retrieve and execute instructions stored in memory, or combinations thereof. The processor can include single or multiple cores on a chip, multiple cores across multiple chips, multiple cores across multiple devices, or combinations thereof. The processor may fetch, decode, and execute instructions from memory to perform various functions. As an alternative or in addition to retrieving and executing instructions, the processor may include at least one integrated circuit (IC), other control logic, other electronic circuits, or combinations thereof that include a number of electronic components for performing various tasks or functions.

Controller 130 may include memory, such as a machine-readable storage medium. The machine-readable storage medium may be any electronic, magnetic, optical, or other physical storage device that contains or stores executable instructions. Thus, the machine-readable storage medium may comprise, for example, various Random Access Memory (RAM), Read Only Memory (ROM), flash memory, and combinations thereof. For example, the machine-readable medium may include a Non-Volatile Random Access Memory (NVRAM), an Electrically Erasable Programmable Read-Only Memory (EEPROM), a storage drive, a NAND flash memory, and the like. Further, the machine-readable storage medium can be computer-readable and non-transitory.

The controller 130 may identify and/or authenticate a user based on the sensed signal. Extractor 132 may extract multiple features of the portion of the user's body from the sensed signal. Classifier 134 may determine, based on the extracted features, whether the portion of the user's body corresponds to a model of the portion of the body used by the classifier. Based on this determination, the user may be identified and/or authenticated.

The classifier 134 may be generated according to various classification techniques in the field of pattern recognition. For example, support vector machines or neural networks may be used. A support vector machine may be appropriate if the model is to be used for user authentication, since support vector machines are binary classifiers. On the other hand, a neural network may be appropriate if the model is to be used for user identification. Other classification techniques may be used as well.

The model used by classifier 134 may be initially generated by training the classifier 134. A process for training the classifier 134 may be initiated by one or more users when the users are configuring computing device 100 for operation. The training process may include taking several sample measurements of the user's body part/portion. Feature extraction and/or feature selection may be used to obtain a number of features that distinctively identify the user based on the measured values of those features from the sample measurements. A model to identify the user may be constructed based on those features.

In the case of user identification, a single model may be constructed based on sample measurements of all of the users such that the model can be used to identify which of any of the users is using the computing device 100. In the case of user authentication, a single model may be constructed for each user to be authenticated. Each model may be constructed based on the sample measurements of the respective user.

Accordingly, the features extracted by extractor 132 may be pre-determined/dictated by the model used by classifier 134 for identifying or authenticating the user. That is, the sensed signal may be parsed to identify a corresponding value/measurement for each feature that makes up the model used by classifier 134. The model may then be used to classify the user by comparing the values/measurements of each extracted feature with the representations of those features in the model. In the case of user identification, the user may be classified as one of the users represented by the model. In the case of user authentication, the user can be classified as being the user represented by the model or as not being the user represented by the model.

Figure 3:
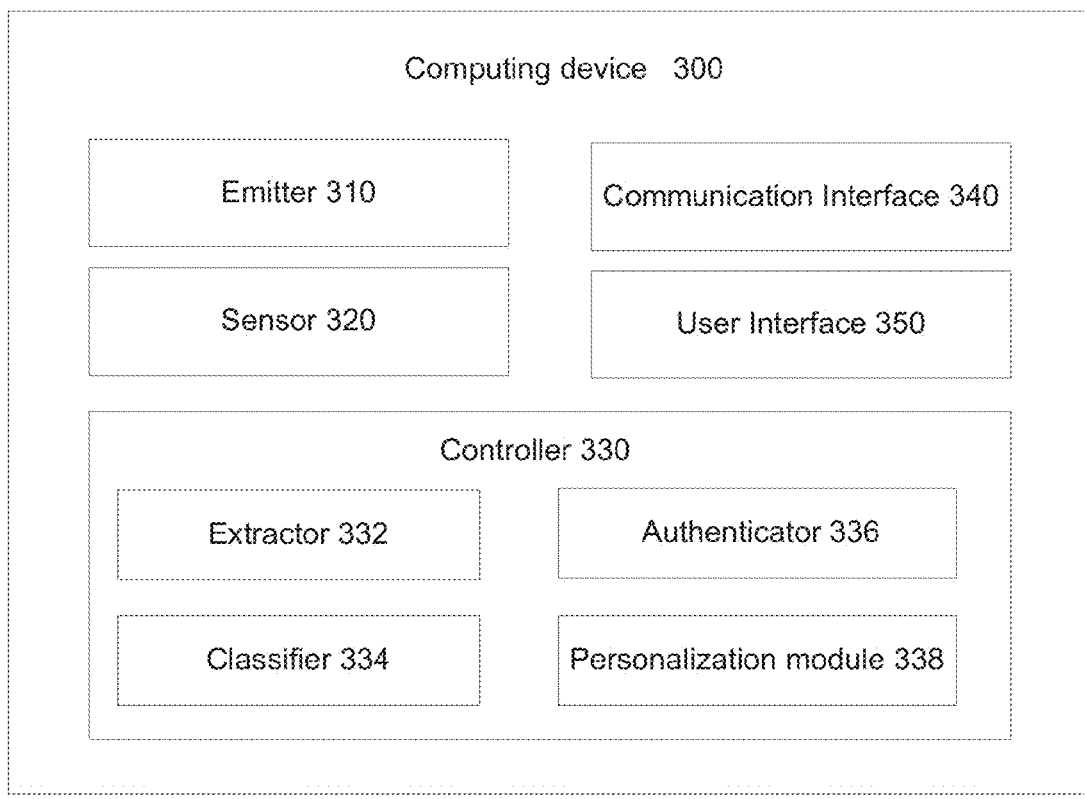
FIG. 3 illustrates a computing device for identifying or authenticating a user, according to an example.

FIG. 3 illustrates a computing device 300 for identifying or authenticating a user, according to an example. The emitter 310, sensor 320, controller 330, extractor 332, and classifier 334 may be configured similar to the corresponding elements in computing device 100.

Computing device 300 may include a communication interface 340. Communication interface 340 may be used to connect to and communicate with other computing devices. Communication interface may include, for example, a transmitter that may convert electronic signals to radio frequency (RF) signals and/or a receiver that may convert RF signals to electronic signals. Alternatively, communication interface 340 may include a transceiver to perform functions of both the transmitter and receiver. Communication interface 340 may further include or connect to an antenna assembly to transmit and receive the RF signals over the air. Communication interface 340 may communicate with a network, such as a wireless network, a cellular network, a local area network, a wide area network, a telephone network, an intranet, the Internet, or a combination thereof. Communication interface 340 may also include an Ethernet connection, a USB connection, or other direct connection to a network or other devices.

In an example, computing device 300 may receive a message from another computing device via communication interface 340. The message may be a request to authenticate the current user of computing device 300. The computing device may be configured to cause emitter 310 to emit a signal in response to the message, so as to verify the identity of the user. The user authentication process may proceed as previously described to verify the current user's identity. Computing device 300 may be configured to send a message to the other device indicating whether the user was authenticated.

Computing device 300 may include a user interface 350. User interface 350 may include hardware, such as a display, a touch sensitive surface, a keyboard, buttons, a microphone, speakers, or the like. User interface 350 may also include software, such as machine-readable instructions for implementing a graphical user interface, a voice command interface, or the like. Furthermore, user interface 350 may include multiple interfaces or a combination of different interfaces.

User interface 350 may be configured to accept an input requesting access to a feature of computing device 300. For example, the input may represent a user's request to access an application of computing device 300. Computing device 300 may be configured to cause emitter 310 to emit a signal in response to the input, so as to verify the identity of or authenticate the user. The user identification/authentication process may proceed as previously described to determine whether the user's request should be granted.

Controller 330 may include an authenticator 336 and a personalization module 338, each of which may be implemented via a software module stored in a memory and executed by a processor of controller 330.

Authenticator 336 may authenticate a user if classifier 334 determines that the portion of the user's body corresponds to the model of the portion of the body used by the classifier. Authenticator 336 may interface with the operating system of computing device 300 to grant permissions to the user that has been authenticated. For example, the permissions may allow the user to access various applications, programs, features, and the like, of computing device 300. Where a user is not authenticated, authenticator 336 may handle the failure in various ways. For example, the user can be prevented from accessing the requested feature. Alternatively, after a predetermined number of failures, computing device 300 may be selectively or completely wiped (e.g., all sensitive data may be erased). Authenticator 338 may also be used to cause a message, which may be a secured message, to be sent via communication interface 340 to another computing device indicating that the user has been authenticated.

Personalization module 338 may store settings for each of a plurality of users. The settings may be stored in user profiles. The settings may relate to settings of computing device 300, such as a contacts list, applications, music, user interface skins, etc. The classifier 334 may determine which user of the plurality of users a current user corresponds to. The personalization module 338 may be configured to cause computing device 300 to implement the settings of the user profile corresponding to the user identified by the classifier 334.

Figure 4:
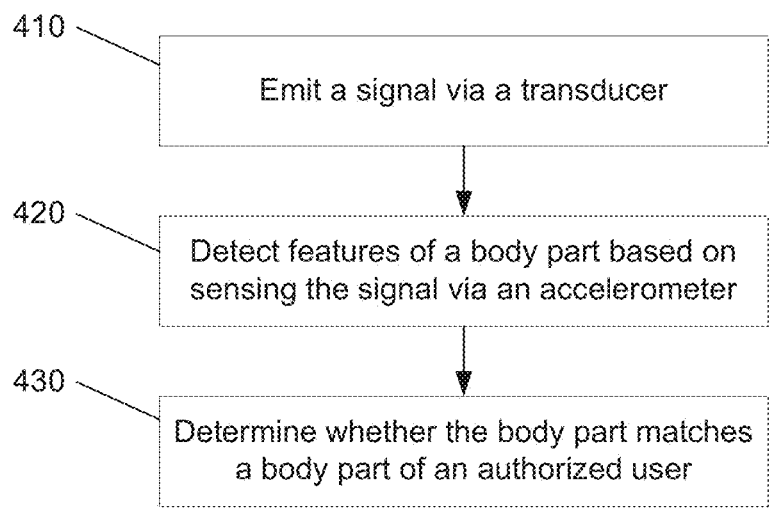
FIG. 4 illustrates a method of identifying or authenticating a user, according to an example.

FIG. 4 illustrates a method 400 of identifying or authenticating a user, according to an example. Method 400 may be implemented by a computing device, such as computing device 100 or 300. At 410, a signal may be emitted via a transducer. The transducer may be in a computing device, such as a smart phone or tablet computer. In an example, the signal may be a vibratory signal. At 420, features of a body part in contact with the computing device may be detected. The features may be detected based on sensing the signal via an accelerometer. The features may be feature vectors for use in pattern recognition. At 430, it may be determined whether the body part in contact with the portable device matches a body part of an authorized person. The determination may be made by inputting the detected features into a pattern recognition model. For example, the pattern recognition model may be a model used by a classifier, such as a support vector machine. Other features, such as described with respect to computing device 100 or 300, may also be implemented as methods.

Figure 5:
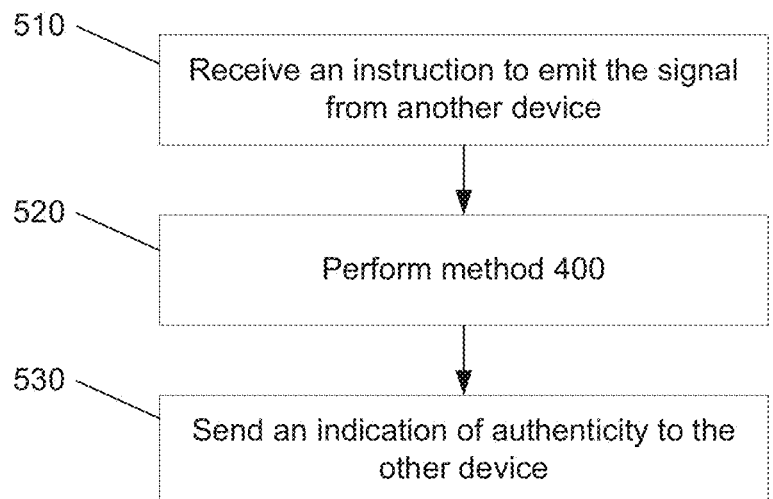
FIG. 5 illustrates a method of authenticating a user, according to an example.

FIG. 5 illustrates a method 500 of authenticating a user, according to an example. At 510, a message may be received from another device. The message may be an instruction to perform an authentication process on the user. Thus, in response to the message, a vibratory signal can be emitted and the authentication process of method 400 may be performed at 520. At 530, an indication of the authenticity of the user may be sent to the other device. Specifically, an indication may be sent to the other device that the current user of the device matches the authorized person if it is determined that the body part in contact with the device matches the body part of the authorized person.

In an embodiment, method 400 or 500 may be performed with respect to more than one body part of a user. The method may be performed with respect to the multiple body parts at the same time or in sequence. For example, for authentication, a user may grip a smart phone by hand and hold the smart phone close to the user's ear. The device may then perform method 400 to sense both the internal structure of the user's hand and the internal structure of the user's ear. Where a single signal is emitted, the device may be configured to sense the signal after a first period of time and a second period of time. The signal sensed after the first period of time may correspond to the structure of the hand. The signal sensed after the second period of time may correspond to the structure of the ear. The sensed signals may then be compared to respective pattern recognition models (e.g., one model representing an authenticated user's hand and the other model representing the authenticated user's ear).

In some examples, additional emitters (e.g., transducers) and sensors (e.g., accelerometers) may be included. For example, a set of headphones may be configured to include an emitter and a sensor for performing the method of 400 on a user's ear. As another example, a patch or band that may be worn over various body parts may be configured to include an emitter and a sensor for performing the method of 400 on various body parts. These additional devices may further be configured to communicate with a primary device, such as computing device 100 or 300, so as to work in concert with the primary device for authentication and identification purposes.

Figure 6:
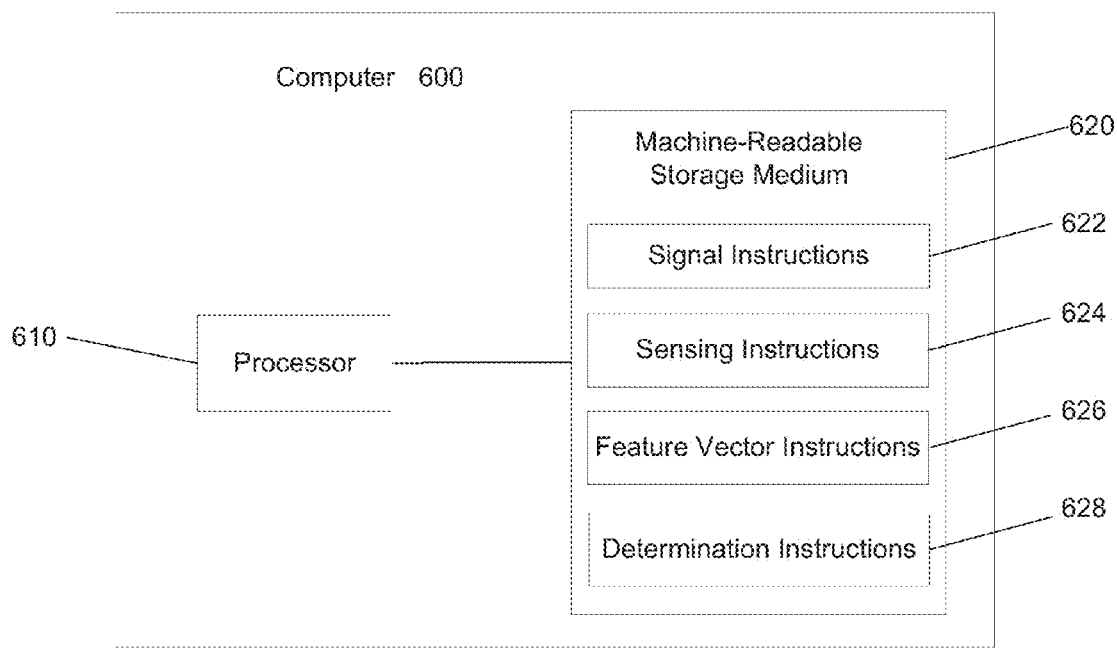
FIG. 6 illustrates a computer-readable medium for implementing user identification or authentication, according to an example.

FIG. 6 illustrates a computer-readable medium for implementing user identification or authentication, according to an example. Computer 600 may be any of a variety of computing devices, such as described with respect to computing device 100.

Processor 610 may be at least one central processing unit (CPU), at least one semiconductor-based microprocessor, other hardware devices or processing elements suitable to retrieve and execute instructions stored in machine-readable storage medium 620, or combinations thereof. Processor 610 can include single or multiple cores on a chip, multiple cores across multiple chips, multiple cores across multiple devices, or combinations thereof. Processor 610 may fetch, decode, and execute instructions 622, 624, 626, 628 among others, to implement various processing. As an alternative or in addition to retrieving and executing instructions, processor 610 may include at least one integrated circuit (IC), other control logic, other electronic circuits, or combinations thereof that include a number of electronic components for performing the functionality of instructions 622, 624, 626, 628. Accordingly, processor 610 may be implemented across multiple processing units and instructions 622, 624, 626, 628 may be implemented by different processing units in different areas of computer 600.

Machine-readable storage medium 620 may be any electronic, magnetic, optical, or other physical storage device that contains or stores executable instructions. Thus, the machine-readable storage medium may comprise, for example, various Random Access Memory (RAM), Read Only Memory (ROM), flash memory, and combinations thereof. For example, the machine-readable medium may include a Non-Volatile Random Access Memory (NVRAM), an Electrically Erasable Programmable Read-Only Memory (EEPROM), a storage drive, a NAND flash memory, and the like. Further, the machine-readable storage medium 620 can be computer-readable and non-transitory. Machine-readable storage medium 620 may be encoded with a series of executable instructions for managing processing elements.

The instructions 622, 624, 626, 628 when executed by processor 610 (e.g., via one processing element or multiple processing elements of the processor) can cause processor 610 to perform processes, for example, the processes depicted in FIGS. 4 and 5. Furthermore, computer 600 may be similar to computing device 100 or 300 and may have similar functionality and be used in similar ways, as described above.

Signal instructions 622 can cause processor 610 to direct a transducer to emit a signal. The signal may be an acoustic signal. Sensing instructions 624 can cause processor 610 to direct an accelerometer to sense the emitted signal after a period of time. Feature vector instructions 626 can cause processor 610 to construct feature vectors representing a body part of an unidentified subject. The feature vectors may be constructed from the sensed signal. Determination instructions 628 can cause processor 610 to determine whether the unidentified subject matches a user based on the feature vectors. For example, the feature vectors may be input to a classifier having a predictive model according to pattern recognition techniques.

What is claimed is:

1. A computing device, comprising:
   an emitter to emit an acoustic signal;
   a sensor to sense the acoustic signal after the acoustic signal has passed through a portion of a user's body;
   an extractor to extract multiple features of the portion of the user's body from the sensed acoustic signal; and
   a classifier to determine, based on the extracted multiple features, whether the portion of the user's body corresponds to a model of the portion of the user's body used by the classifier.

2. The computing device of claim 1, further comprising an authenticator to authenticate the user in response to the classifier determining the portion of the user's body corresponds to the model of the portion of the user's body used by the classifier.

3. The computing device of claim 1, further comprising a communication interface, wherein the computing device is to cause the emitter to emit the acoustic signal in response to a message received by the communication interface from a second computing device requesting authentication of the user.

4. The computing device of claim 1, further comprising a user interface to accept an input requesting access to a feature of the computing device, wherein the computing device is to cause the emitter to emit the acoustic signal in response to the input.

5. The computing device of claim 1, wherein the classifier is configured to determine which user profile of a plurality of user profiles the user corresponds to based on the extracted multiple features.

6. The computing device of claim 5, further comprising a personalization module to store settings for each of the plurality of user profiles, the personalization module configured to implement the settings of a respective user profile of the plurality of user profiles on the computing device in response to the classifier determining that the user corresponds to the respective user profile.

7. The computing device of claim 1, wherein the portion of the user's body is a hand.

8. A method, comprising:
   emitting a vibratory signal via a transducer of a portable device;
   detecting features of a body part in contact with the portable device based on sensing the vibratory signal via an accelerometer; and
   determining whether the body part in contact with the portable device matches a body part of an authorized person by inputting the detected features into a pattern recognition model.

9. The method of claim 8, wherein the detecting comprises detecting features of plural body parts in contact with the portable device based on sensing the vibratory signal via the accelerometer, and wherein the determining comprises determining whether the plural body parts in contact with the portable device match plural body parts of the authorized person by inputting the detected features into respective pattern recognition models.

10. The method of claim 8, further comprising:
    receiving an instruction to emit the vibratory signal from another device; and
    sending an indication to the another device that a user of the portable device matches the authorized person in response to determining that the body part in contact with the portable device matches the body part of the authorized person.

11. The method of claim 8, further comprising granting access to a feature of the portable device in response to determining that the body part in contact with the portable device matches the body part of the authorized person.

12. The method of claim 8, wherein the detected features are based on the vibratory signal after reflection from a physical structure of the body part.

13. The method of claim 8, wherein the detected features are based on the vibratory signal after transmittance through a physical structure of the body part.

14. The method of claim 8, wherein the pattern recognition model is a support vector machine.

15. A non-transitory computer-readable storage medium comprising instructions that, when executed by a processor, cause the processor to:
   instruct a transducer to emit an acoustic signal;
   receive a sensed acoustic signal detected by an accelerometer in response to the acoustic signal after the acoustic signal has passed through a body part of an unidentified subject;
   construct feature vectors representing the body part of the unidentified subject from the sensed acoustic signal; and
   determine whether the unidentified subject matches a user based on the feature vectors.

16. The computing device of claim 1, further comprising a housing, wherein the emitter and the sensor are contained in the housing.

17. The computing device of claim 1, wherein the acoustic signal is a vibratory signal, and the sensor is to sense the vibratory signal after the vibratory signal has passed through the portion of the user's body, and the extracted multiple features are based on the sensed vibratory signal.

18. The computing device of claim 3, wherein the communication interface is to send, to the second computing device in response to the message, an indication that the user has been authenticated based on determining by the classifier that the portion of the user's body corresponds to the model of the portion of the user's body.

19. The non-transitory computer-readable storage medium of claim 15, wherein the processor is contained in a housing of a portable device, and the transducer and the accelerometer are also contained in the housing.

20. The non-transitory computer-readable storage medium of claim 15, wherein the acoustic signal is a vibratory signal, and the accelerometer is to sense the vibratory signal after the vibratory signal has passed through the body part, and the constructed feature vectors are based on the sensed vibratory signal.

* * * * *

UNITED STATES PATENT AND TRADEMARK OFFICE
CERTIFICATE OF CORRECTION

PATENT NO. : 9,609,511 B2  
APPLICATION NO. : 14/394513  
DATED : March 28, 2017  
INVENTOR(S) : Esra Vural et al.

Page 1 of 1

It is certified that error appears in the above-identified patent and that said Letters Patent is hereby corrected as shown below:

On the Title Page

Item (75), Inventors, in Column 1, Line 2, delete "Corvailis," and insert -- Corvallis, --, therefor.

In the Claims

In Column 8, Line 18, in Claim 2, delete "determining the" and insert -- determining that the --, therefor.

Signed and Sealed this  
Fourth Day of July, 2017

Joseph Matal  
*Performing the Functions and Duties of the*  
*Under Secretary of Commerce for Intellectual Property and*  
*Director of the United States Patent and Trademark Office*